United States Patent
Poirier (10) Patent No.: US 10,744,258 B1
(45) Date of Patent: Aug. 18, 2020

(54) DEVICES AND METHODS FOR ON-LINE WHOLE BLOOD TREATMENT

(71) Applicant: Qualigen Inc., Carlsbad, CA (US)

(72) Inventor: Michael Poirier, Vista, CA (US)

(73) Assignee: Qualigen Inc., Carlsbad, CA (US)

( * ) Notice: Subject to any disclaimer, the term of this patent is extended or adjusted under 35 U.S.C. 154(b) by 293 days.

(21) Appl. No.: 15/913,729

(22) Filed: Mar. 6, 2018

Related U.S. Application Data (60) Provisional application No. 62/467,408, filed on Mar. 6, 2017.

(51) Int. Cl.
| | | |
|---|---|---|
| *A61M 5/00* | (2006.01) |
| *A61M 5/165* | (2006.01) |
| *B01D 15/38* | (2006.01) |
| *B01D 15/18* | (2006.01) |

(Continued)

(52) U.S. Cl.
CPC .......... *A61M 5/165* (2013.01); *A61M 27/002* (2013.01); *B01D 15/1892* (2013.01); *B01D 15/203* (2013.01); *B01D 15/3809* (2013.01); *B01D 15/3823* (2013.01); *A61M 2202/049* (2013.01); *A61M 2202/0447* (2013.01); *A61M 2202/203* (2013.01); *A61M 2202/206* (2013.01);

(Continued)

(58) Field of Classification Search
CPC ................ A61M 5/165; A61M 27/002; A61M 2005/1652; A61M 2005/1655; A61M 2005/1657; A61M 2202/0447; A61M 2202/049; A61M 2202/203; A61M 2202/206; A61M 2005/103; A61M 2005/106; A61M 2005/3344; A61M 2206/14; A61M 2209/088; B01D 15/1892; B01D 15/203; B01D 15/3809; B01D 15/3823; B01D 2215/022
See application file for complete search history.

(56) References Cited

U.S. PATENT DOCUMENTS

| | | |
|---|---|---|
| 6,143,510 A | 11/2000 | Hoshino et al. |
| 7,214,544 B2 | 5/2007 | Poirier et al. |

(Continued)

FOREIGN PATENT DOCUMENTS

WO 2011/005742 1/2011

OTHER PUBLICATIONS

Ghirelli, C. et al., "Targeting immunosuppression for cancer therapy", The Journal of Clinical Investigation, vol. 123, No. 6, pp. 2355-2357, (2013).

(Continued)

*Primary Examiner* — Philip R Wiest
(74) *Attorney, Agent, or Firm* — Evan Law Group LLC (57) ABSTRACT

A whole blood treatment device includes a first conduit, a second conduit, and a rotating or reciprocating element having a channel. The first and second conduits are fluidly coupled to the rotating or reciprocating element such that the channel is fluidly continuous with the first conduit when the channel is fluidly discontinuous with the second conduit, and such that the channel is fluidly discontinuous with the first conduit when the channel is fluidly continuous with the second conduit. The first conduit is configured to receive whole blood, and the second conduit is configured to receive a regeneration fluid. The channel comprises a surface that is modified with an affinity agent at a concentration effective to allow removal of a target compound from whole blood.

20 Claims, 3 Drawing Sheets

(51) Int. Cl.
*B01D 15/20* (2006.01)
*A61M 27/00* (2006.01)

(52) U.S. Cl.
CPC . *A61M 2205/103* (2013.01); *A61M 2205/106* (2013.01); *A61M 2205/3344* (2013.01); *A61M 2206/14* (2013.01); *A61M 2209/088* (2013.01); *B01D 2215/022* (2013.01)

(56) References Cited

U.S. PATENT DOCUMENTS

| | | | |
|---|---|---|---|
| 7,754,499 | B2 | 7/2010 | Poirier et al. |
| 2009/0114595 | A1* | 5/2009 | Wallenas ............ A61M 1/1696 210/646 |

OTHER PUBLICATIONS

Focosi, D. et al., "Immunosuppressive monoclonal antibodies: current and next generation", Clinical Microbiology and Infection, vol. 17, pp. 1759-1768, (2011).

Chan, A.C. et al., "Therapeutic antibodies for autoimmunity and inflammation", Nature Reviews Immunology, vol. 10, pp. 301-316, (2010).

Zhang, X-B., et al., "Metal ion sensors based on DNAzymes and related DNA molecules", Annual Review of Analytical Chemistry, vol. 4, No. 1, pp. 105-128, (2011).

Hotchkiss, R.S. et al., "Immunosuppression in sepsis: a novel understanding of the disorder and a new therapeutic approach", The Lancet Infectious Diseases, vol. 13, No. 3, pp. 260-268, (2013).

"Monoclonal antibodies to treat cancer", American Cancer Society, found at www.cancer.org/treatment/treatments-and-side-effects/treatment-types/immunotherapy/monoclonal-antibodies.html, pp. 1-5, Printed on Mar. 21, 2019.

Zhou, Q. et al., "Aptamer-containing surfaces for selective capture of CD4 expressing cells", Langmuir, vol. 28, No. 34, pp. 12544-12549, (2012).

Definition of "Monoclonal antibody therapy" printed from Wikipedia, the free encyclopedia, found at en.wikipedia.org/wiki/Monoclonal_antibody_therapy, Downloaded on Feb. 2, 2017.

* cited by examiner

DEVICES AND METHODS FOR ON-LINE WHOLE BLOOD TREATMENT

FIELD OF THE INVENTION

The field of the invention is treatment of whole blood, especially as it relates to in vivo continuous removal of one or more components contained in whole blood.

BACKGROUND

Removal of various undesirable components from whole blood is well known and often includes ex vivo separation of cellular components (e.g., centrifugation or filtration) to obtain a cell-free fluid that is then processed, typically using affinity media and/or enzymatic treatment. While such treatment is standard practice in many instances, hemolysis is often a problem. Still more disadvantageously, such known treatment typically requires relatively large equipment and is therefore impractical in ambulatory use.

Further known methods for binding of a contaminant from a fluid are described in WO 2011/005742 where a sorbent medium is modified and combined with the fluid. However, the sorbent medium must be separated from cellular components, which is in most cases not feasible to the required degree. To assist in separation of the sorbent, magnetic beads can be used as is described in U.S. Pat. No. 6,143,510. However, such methods are generally limited to ex vivo tests as residual quantities of magnetic beads are highly undesirable. To circumvent problems associated with removal of sorbent, selective permeable membranes may be employed as taught in US 2009/0114595. While such removal is conceptually simple, separation efficiency is in at least some cases less than desirable, especially where large molecules are separated. Thus, there is still a need to provide improved whole blood separation devices and methods.

SUMMARY OF THE INVENTION

The present inventive subject matter is directed to diagnostic and therapeutic devices in which whole blood is passed through one or more channels of a rotating or reciprocating element wherein the channels comprise an affinity agent to allow specific binding of a target compound to the channel. Due to the rotating or reciprocating motion of the element, the channel can be moved into and out of fluid communication with the circulatory system of a mammal such that the affinity agent binds the target compound when the channel is in fluid communication with the circulatory system and such that bound target antigen can be removed from the affinity agent when the channel is removed from the fluid communication with the circulatory system and in fluid communication with a regeneration circuit.

In one aspect of the inventive subject matter, the rotating or reciprocating element has multiple channels and is configured as a rotating wheel, and multiple conduits are separately provided to the channels in the wheel to allow concurrent adsorption of the target compound to one channel while regenerating the affinity agent in another channel. Alternatively, the element may also be configured as an Archimedean screw or a reciprocating piston. Consequently, it should be recognized a target compound can be continuously removed from the blood stream on-line and in vivo as such devices and methods allow for multiple passes of whole blood through the device without saturating the affinity agent.

Various objects, features, aspects and advantages of the present invention will become more apparent from the following detailed description of preferred embodiments of the invention.

Most typically, contemplated devices will therefore include a first conduit, a second conduit, and a rotating or reciprocating element having a channel, wherein the first and second conduits are fluidly coupled to the rotating or reciprocating element such that the channel is fluidly continuous with the first conduit when the channel is fluidly discontinuous with the second conduit, and such that the channel is fluidly discontinuous with the first conduit when the channel is fluidly continuous with the second conduit. The first conduit is preferably configured to receive whole blood (directly from the circulation in an on-line mode, or indirectly, via blood collection bag or other implement), and the second conduit is preferably configured to receive a regeneration fluid (typically from a reservoir or device that prepares the regeneration fluid in situ). Regardless of the particular configuration, the channel will have a surface that is modified with an affinity agent (most typically an antibody or antibody fragment, a nucleic acid or nucleic acid analog, a lectin, etc.) at a concentration effective to allow removal of a target compound from whole blood, wherein the target compound is capable of binding with high specificity and affinity to the affinity agent.

Figure 1A:
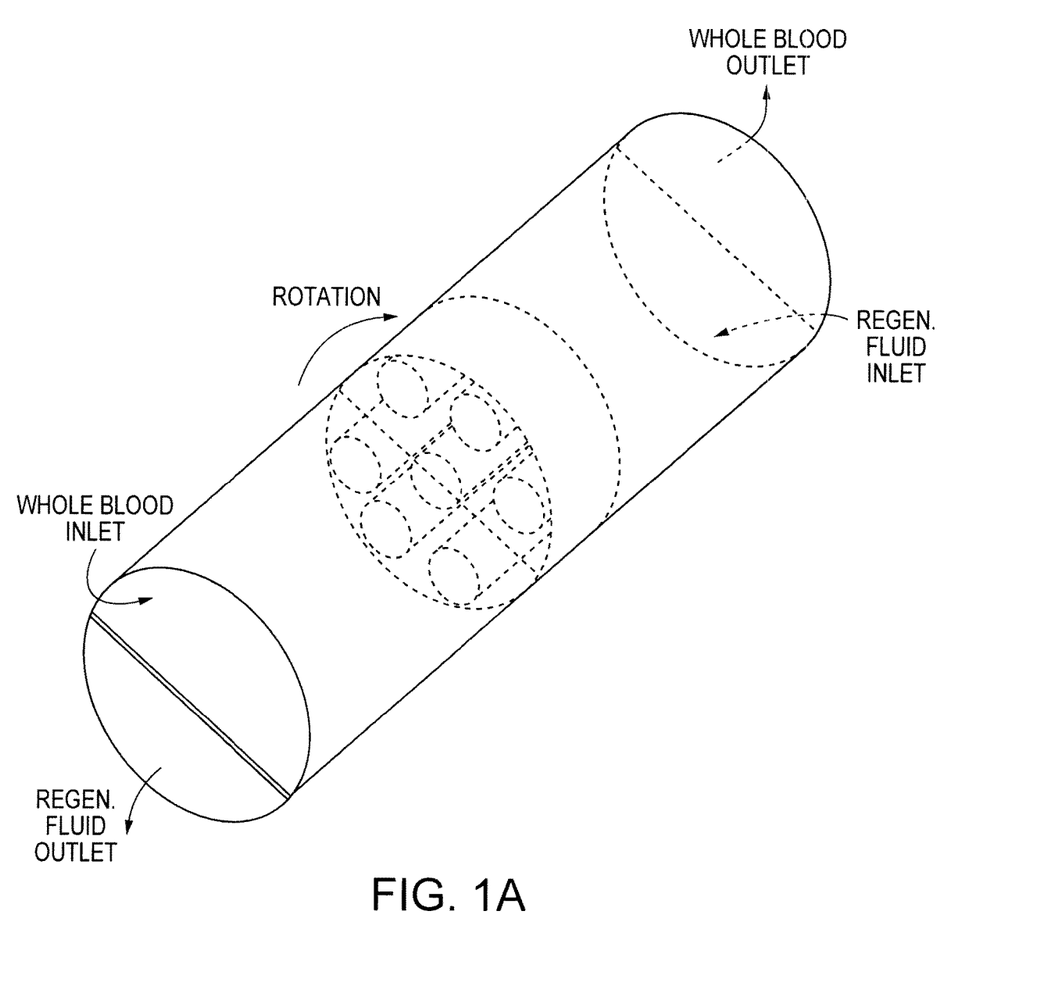

FIG. 1A depicts an exemplary device in which the rotating or reciprocating element is configured as a wheel having a plurality of conduits extending through the wheel. The wheel is preferably rotatably coupled to at least two conduits, which are here indicated as half-pipes with abutting surfaces to so form a cylindrical structure. In the example of FIG. 1A, the wheel is disposed in the middle of the conduits such that flow of whole blood enters the upper conduit at the site marked 'whole blood inlet', passes through the upper three channels that are coated with an antibody (e.g., specific against IL-8), and continues to flow through the upper half-pipe to exit at the site marked 'whole blood outlet'. During this pass, target compounds will bind to the affinity agents. Similarly, and preferably at the same time, flow of regeneration fluid enters the lower conduit at the site marked 'regen fluid inlet', passes through the lower three channels and causes the bound target compounds to elute into the regeneration fluid, which flows through and exits the lower half-pipe to leave the pipe at the site marked 'regen fluid outlet'.

It should be appreciated that the wheel will rotate during operation, preferably at a speed that will allow saturation of the affinity agents with the target compound during the presence of the channel in the upper half-pipe. Once saturated, and due to the preferably continuous rotation of the wheel, the channel with the saturated affinity agents will enter the lower half-pipe and is then exposed to the regeneration fluid for regeneration of the affinity agent. Once regenerated, and due to the preferably continuous rotation of the wheel, the channel with the regenerated affinity agents will enter the lower half-pipe and is once again available for a new cycle of binding and regeneration.

Figure 1B:
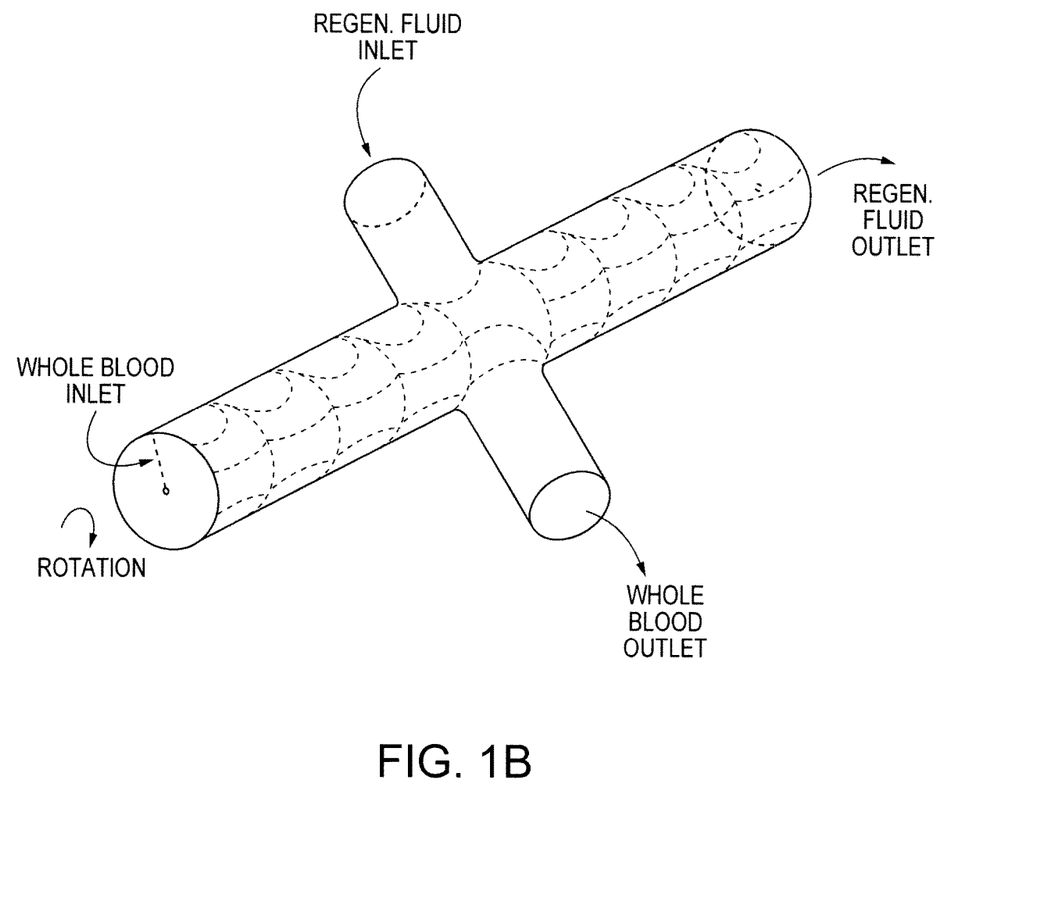

Alternatively, and as depicted in FIG. 1B, the rotating or reciprocating element is configured as a Archimedean screw that fittingly extends through the length of a cylindrical main pipe. At about the middle of the pipe, two fluid conduits join the main pipe in a manner such that (a) fluid entering on one branch of the main pipe is pumped along the pipe and exits one of the two joining conduits, and (b) fluid entering the other of the two joining conduits is pumped into and along the other branch and exits the other branch. In this example, the channel is formed by the helical groove of the screw and is also coated with (or otherwise coupled to) an affinity agent. Thus, in the example of FIG. 1B, whole blood flows through one branch of the main pipe for adsorption of the target compound, while at the same time regeneration fluid flows through the other main branch for regeneration of the affinity agent. Flow of the whole blood and the regeneration fluid is then alternatingly controlled such that when the affinity agents are saturated in one branch, whole blood flow is routed to the other branch that is now regenerated. Regeneration fluid is then routed to the saturated channel to regenerate the binding surface. Viewed from a different perspective, the operational mode between binding and regeneration is switched by switching flow though the device.

Figure 1C:
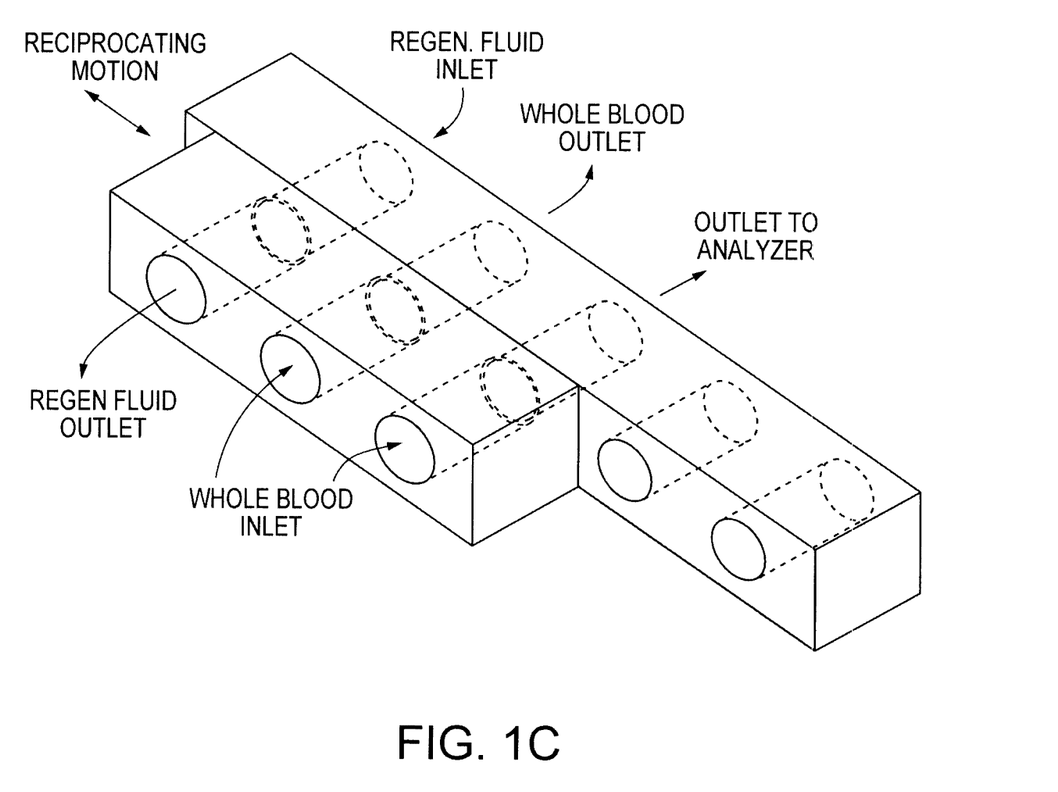

Alternatively, the moving element may also be configured as a reciprocating piston with one or more channels extending through the piston as exemplarily illustrated in FIG. 1C. Here, the piston has a plurality of channels where two channels are concurrently employed for binding and absorption. In this example, the regenerated channel is moved into the flow of whole blood as the binding channel is saturated. FIG. 1C shows an additional channel which may be employed for measurement of an analyte and/or dispensation of a pharmaceutical agent. Once more, it should be appreciated that binding and regeneration can be performed continuously and that such systems are particularly useful for continuous on-line separation of a target compound from whole blood.

Consequently, it should be recognized that method of removing a target compound from whole blood of a mammal is contemplated. More specifically, contemplated methods include a step of moving the whole blood through a channel in a rotating or reciprocating element while the channel is fluidly coupled to a first conduit that contains the whole blood, wherein the channel comprises a surface that is modified with an affinity agent at a concentration effective to allow removal of a target compound from whole blood. In another step, the rotating or reciprocating element is moved into a position such that the channel is fluidly disconnected from the first conduit and fluidly connected with a second conduit, and in yet another step, the target compound is eluted from the surface while the channel is fluidly connected with the second conduit. The rotating or reciprocating element is then further moved into a position such that the channel is fluidly connected with the first conduit and fluidly disconnected with the second conduit.

While it is in most aspects preferred that the affinity agent in contemplated devices and methods is continuously or intermittently regenerated, it should also be appreciated that the affinity agent may be saturated and then discarded (e.g., via user replacement of the rotating or reciprocating element, or via replacement of the channel where the channel is configured as a cylinder). Consequently, another embodiment of a whole blood treatment device may include a first conduit, a sealing area, and a rotating or reciprocating element having a channel, wherein the first conduit is fluidly coupled to the rotating or reciprocating element such that the channel is fluidly continuous with the first conduit when the channel is fluidly discontinuous with the sealing area, and such that the channel is fluidly discontinuous with the first conduit when the channel is fluidly continuous with the sealing area. In such devices, the first conduit is configured to receive whole blood, and the sealing area is configured to allow flow-less incubation of the whole blood in the channel when the channel is fluidly continuous with the sealing area. Thus, and viewed from a different perspective, a volume of whole blood is captured in the channel while the channel is in contact with the sealing area to so allow binding of a target compound from an essentially non-moving or non-flowing volume of whole blood. Such incubation is considered to improve binding efficiency, especially where the volume-to-surface ratio is relatively high. As noted before, the channel will include a surface that is modified with an affinity agent at a concentration effective to allow removal of a target compound from whole blood. Where desirable, the rotating or reciprocating element is disposable and/or user-replaceable, and/or the channel is configured as a replaceable cylinder.

Typical non-regenerating devices are similar to the devices shown in FIG. 1A-1C, however, will not provide second conduits for regeneration fluid. For example, the second conduit in the device of FIG. 1 is entirely omitted and a sealing plate or other sealing implement will seal off the lower conduit. Similarly, the Archimedean screw configuration of FIG. 1B is simplified in that the perpendicular in- and outlet ports can be omitted. In such case, it is generally preferred that two linear conduits will have two independent Archimedean screws with one screw operating while the other screw is not operating and replaceable. Increased incubation time is then achieved by discontinuous rotation, or by addition of a second (third, or higher) screw that operates in a parallel and alternating mode. In the device of FIG. 1C, the device configuration is again simplified by providing one or more flow channels through the reciprocating block. Reciprocating movement of the block will then position a volume of whole blood in a channel between sealing surfaces for a predetermined time to allow longer incubation, and reversal of that movement (or additional forward movement) will then move the treated volume back into circulation.

It is especially preferred that contemplated devices are configured to be wearable, and that the reciprocating or rotating element can be readily exchanged, preferably by a non-medical professional (e.g., end user or caretaker). Thus, in especially preferred aspects, the device has a housing that encloses at least partially the element and conduits. Fluid lines from the patient's circulation and/or regeneration fluid are preferably attachable via luer lock or other suitable connector that preferably allows maintaining sterile working conditions. Moreover, where the device is configured as a user-wearable device, the regeneration fluid (and other fluids, including wash fluids) are preferably also in a wearable format, and most preferably flexible pouches.

In further preferred aspects of the inventive subject matter, it should be appreciated that the device may include more than one rotating or reciprocating element and/or that there are more than one type of affinity agent in one or more channels. Likewise, it should be recognized that contemplated devices and methods are not limited to those having only two conduits, but any number of conduits are deemed suitable. Additional conduits may be used for measurement of one or more analytes in the whole blood and/or the regeneration fluid, and/or for provision of wash fluids and/or pharmaceutical agent. Of course, contemplated device may also implement additional functionalities using a flow splitter that may be upstream or downstream, of the wheel (with respect to the flow of the whole blood). The so produced bypass or slipstream can then be treated or analyzed as desired, and fed back to the circulation or be discarded into a typically disposable waste container.

While continuous flow of whole blood through the device is generally preferred, it is also contemplated that intermittent flow may be directed through the device. In such case, or where a stop valve is activated in the flow path, the conduit may include or may be coupled to a surge compartment to accommodate discontinuous flow and to maintain constant flow rate through the device. Thus, contemplated devices may have a continuously operating pump, a pump that operates in on-off mode, or no pump at all. Thus, the whole blood may be driven by an active pump (e.g., peristaltic, piston, etc.), or passively by a blood pressure driven mechanism. Similarly, it is generally preferred that the reciprocating or rotating element is actuated by a motor or other actuator, preferably in a continuous manner at constant speed. However, where desirable, the speed of the rotating or reciprocating element may also be variable and/or in an intermittent pattern.

The number and geometry of channel may vary considerably and will predominantly be determined by the desired flow rate of whole blood through the element, the quantity of target compound in the whole blood, and affinity of the target compound. It is generally preferred that the channels are formed to reduce or even entirely avoid turbulent flow. Thus, channels are preferably linear or helical with a larger-than-capillary diameter (e.g., at least 50 micron, more preferably at least 100 micron, and most preferably at least 250 micron). It is further noted that the transition of a channel from blood to regeneration fluid may include a rinse step in the device and/or via a flow loop with one or more valves. Thus, most preferably, loss of whole blood is avoided as the volume of whole blood in the channel may be recycled back to the mammal (e.g., using isotonic fluid as a wash fluid).

Sealing of the movable element against fluid and blood loss can be achieved in numerous manners well known in the art. For example, rotary seals, rubber lip seals, or bore seals with O-rings are deemed suitable for use herein. Similarly, press-fit tolerance may be employed to reduce leakage of the channel/conduit interface.

Many various target compounds can be targeted for removal from the blood, and various affinity agents can be used, where the affinity agents have a binding affinity to the target compound to be removed. The inventors have now discovered that chemotherapy compliance can be significantly improved when IL-8 and/or CRP concentrations are reduced in whole blood of a patient that is treated with a drug that increases at least one of IL-8 and/or CRP. In especially preferred aspects, IL-8/CRP reduction is performed on-line in a continuous manner using a wearable device, such as the device described herein. The device can be used to remove other antigens and small molecules from whole blood by passing the blood through channels, which comprise an affinity agent to bind to the target compound.

In one particularly preferred aspect of the inventive subject matter, IL-8 and CRP levels are elevated in whole blood of a patient undergoing taxane (e.g., paclitaxel or decetaxel) chemotherapy, for example, in the treatment of pancreatic cancer. Such treatment may be in combination with other drugs, for example, gemzitabine. Most typically, chemotherapy in such and similar cases is not well tolerated and a significant fraction of patients will discontinue treatment due to the severe side effects.

The inventors have determined that IL-8 and CRP levels in patients about to discontinue chemotherapy is well above normal reference ranges, typically at least 25%, and most typically at least 50% above the upper range of normal, and contemplate that continuous reduction of the elevated levels, preferably back to reference range, will increase the level of compliance. It is generally preferred that the continuous treatment will extend over a period of at least 12 hours, more typically at least 24 hours, and most typically over at least 3 days. Thus, and viewed from another perspective, it is contemplated that the reduction of IL-8 and/or CRP will be effected over a period that coincides with at least a portion of time over which elevated levels will be observed without treatment.

In this context, it should be noted that the reduction of IL-8 and/or CRP is not intended as a treatment modality of the underlying disease, but as a palliative treatment of a condition that is brought about by pharmacological intervention. Thus, methods presented herein are targeted to improve subjective well-being of a patient, and especially relieve nausea, flu-like symptoms, loss of appetite, and physical and/or metal fatigue.

However, and with respect to the disease being treated, it should be appreciated that any disease that requires drug treatment, and/or any disease that is characterized by excessive blood concentrations of IL-8 and/or CRP is contemplated herein. For example, contemplated methods may be effective not only in combating side effects of chemotherapy of various neoplastic diseases, but also infectious diseases and especially including viral diseases (and particularly influenza virus, H1N1 flu, SARS, etc.), chronic inflammatory diseases (e.g., COPD, rheumatoid arthritis, inflammatory bowel disease, psoriasis, etc.), atherosclerosis, and acute coronary syndrome.

Consequently, and depending on the particular nature of disease or treatment, it should be appreciated that the chemotherapeutic agent may vary considerably. Most typically, however, the pharmaceutical treatment will include chemotherapy for various neoplastic diseases, and especially those agents that are known to be associated with an increase in IL-8 and/or CRP. For example, contemplated chemotherapies may include administration of one or more of receptor antibodies, alkylating agents, antimetabolites, microtubule inhibitors (and especially taxanes), topoisomerases, and kinase inhibitors. Similarly, contemplated methods may be implemented on an intermittent or continuous basis, and it is generally contemplated that the reduction in IL-8 and/or CRP is performed as long as excessive levels of IL-8 and/or CRP are measured or anticipated. For example, where administration of a chemotherapeutic agent results in a relatively broad and temporary spike in blood IL-8 levels (e.g., over 2 days), reduction of IL-8 may be performed in a continuous manner over two days. On the other hand, where the increase is relatively brief, reduction may be performed in a discontinuous manner immediately following administration of the chemotherapeutic agent. On the other hand, where the elevated levels of IL-8 and/or CRP are, for example, due to a chronic inflammatory condition, continuous reduction in IL-8 and/or CRP may be advisable.

Removal is preferably monitored to achieve a continuous IL-8 and/or CRP level that is within the normal reference range (and in some cases below or slightly above). For example, the clinical range of IL-8 is typically between 10-80 pg/ml for a healthy person, and it is typically preferred that reduction of IL-8 is to equal or less than 100 pg/ml, and more preferably to equal or less than 80 pg/ml. Similarly, the clinical normal range for CRP is between 0-5 mg/l for male and 0-8 for female healthy adults, and it is typically preferred that reduction of CRP is to equal or less than 5 mg/l, more preferably to equal or less than 3 mg/l, and most preferably to equal or less than 1 mg/l.

Reduction of IL-8 and/or CRP is preferably effected via specific antibodies (e.g., HuMab 10F8 for IL-8), or other known IL-8 binders, including glycosaminoglycan (GAG) heparin, protease inhibitor alpha2-macroglobulin, Cyclosporin A, however, engineered binding agents are also deemed suitable, including recombinant IL-8 receptor and fragments thereof. Similarly, it is contemplated that CRP can be reduced by binding of CRP to one or more types of monoclonal or polyclonal antibodies, Fc receptors (e.g., FcγRIIa), etc., and the number of binding agents needed to reduce the IL-8 and/or CRP levels will preferably be chosen such that continuous treatment for at least 2, and more typically 4 consecutive days is possible without patient intervention.

The device may also be used to target other cellular components and extracellular components, such as proteins, fats and small molecules, and may also be used to target cells. The whole blood treatment device can also be used to treat various diseases that are caused by one or more target compounds. Examples of these disease include treating cancer by reducing inhibitory checkpoint molecules or removing cancer cells, autoimmune diseases by reducing inflammatory factors, cardiovascular disease by reducing low-density lipoprotein, metabolic diseases such as diabetes by reducing glucose, viral infection and bacterial infection by reducing the amount of virus, bacteria or associated toxin, and toxin exposure and heavy metal exposure by removing the toxin or heavy metal. Such diseases may be treated with the device by determining a target compound that can be removed from the body, and determining an affinity agent that binds to the target compound. Antibodies or aptamers suited to binding the selected target compound could be used as the affinity agents, but it is understood that other compounds could also be used.

Inhibitory checkpoint molecules are secreted by cancer cells to reduce the immune response. There are several antibody drugs (referred to as immune checkpoint inhibitors or immune checkpoint blockades) that target these inhibitory checkpoint molecules in order to increase the immune response to cancer cells. Rather than using these antibodies as a drug, the whole blood treatment devices pass whole blood through channels with a surface modified with affinity agents, where the inhibitory checkpoint molecules are bound by the affinity agents, and removed from the blood, reducing the concentration of inhibitory checkpoint molecules in the blood. Some examples of inhibitory checkpoint molecules are cytotoxic T-lymphocyte associated protein 4 (CTLA-4), programmed cell death-1 (PD-1), programmed death-ligand 1 (PD-L1), B7-1, B7-2, $FOXP3^+$, $FOXP3^-$, Treg 17, Tr1, Th3, IL-10, and TGF-β. Some examples of antibody drugs that could be used as affinity agents include ipilimumab, ticilimumab, pembrolizumab, atezolizumab and nivolumab, along with many others, as described in Ghirelli et al. ("Targeting immunosuppression for cancer therapy" J Clin Invest. 2013; 123(6):2355-2357.).

Inflammatory factors are often reduced using antibody drug treatments. Rather than administering antibodies as drugs, these same antibodies can be used in the channels of the whole blood treatment devices to bind inflammatory factors to reduce the concentration of inflammatory factors in the blood. Inflammatory factors may include IL-4, IL-10, TNFα, IL-17A, IL-17F, CRP, TNF, IL-1α, IL-1β, IL-5, IL-6, IL-8, IL-12, IL-23, CD2, CD3, CD20, CD22, CD52, CD80, CD86, C5 complement protein, BAFF, APRIL, IgE, α4rβ1 integrin and α4β7 integrin. These inflammatory factors may be bound by IL-17A/F antibodies, abatacept, alefacept, alemtuzumab, atacicept, belimumab, canakinumab, eculizumab, epratuzumab, natalizumab, ocrelizumab, ofatumumab, omalizumab, otelixizumab, rituximab, teplizumab, vedolizumab, adalimumab, briakinumab, certolizumab pegol, etanercept, golimumab, infliximab, mepolizumab, reslizumab, tocilizumab and ustekinumab. Other antibodies or aptamers could also be used to target inflammatory factors as shown in Focosi et al. ("Immunosuppressive monoclonal antibodies: current and next generation" Clin Microbiol Infect 2011; 17: 1759-1768) and Chan, A. C. et al. ("Therapeutic antibodies for autoimmunity and inflammation", Nature Reviews Immunology, vol. 10, pp. 301-316, (2010)). Diseases that could be treated by targeting inflammatory factors include asthma, rheumatoid arthritis, autoimmune disorders and gastrointestinal diseases.

Viruses can be targeted using various drugs. However, removing these from the blood, via a whole blood treatment device would reduce unintended side effects. The target compounds can include viruses and cells infected with viruses. Examples of viruses include chickenpox, flu (influenza), herpes, human immunodeficiency virus (HIV/AIDS), human papillomavirus (HPV), infectious mononucleosis, mumps, measles, rubella and shingles. Antibodies that bind to these viruses may be used as the affinity agent, and can be prepared by well-known methods.

Antibodies can be used to treat various cancers. Rather than using antibodies that bind cancer cells as a drug, these antibodies can be used in a channel of a whole blood treatment device. Examples of cancer cells include skin, breast, lung, pancreas, kidney, leukemia, lymphoma, and many other types of cancer. For example, treatment of cancer can be carried out by targeting cells displaying nucleolin on the cell surface. Anti-nucleolin antibodies can bind to the nucleolin on the surface of the cancer cell. Various anti-nucleolin antibodies include p7-1A4 mouse monoclonal antibody, sc-8031 mouse mAb, sc-9893 goat polyclonal Ab (pAb), sc-9892 goat pAb, clone 4E2 mouse mAb, and clone 3G4B2 mouse mAb, which may be used as affinity agents. Other examples of antibody drugs to treat cancer cells, which may be used as affinity agents include alemtuzumab, trastuzumab, Ibritumomab tiuxetan, Brentuximab vedotin, Ado-trastuzumab emtansine, denileukin diftitox, and blinatumomab, along with other can be found in American Cancer Society; Monoclonal Antibodies to Treat Cancer (available at www.cancer.org/treatment/treatments-and-side-effects/treatment-types/immunotherapy/monoclonal-antibodies.html). Other drugs may be used to bind cancer cells within the device.

Heavy metal poisoning may be treated with a whole blood treatment device to reduce the concentration of heavy metals to a safe level. Heavy metals may include lead, mercury, arsenic and cadmium. These metals can be bound by an affinity agent such as DNAzyme as described in Zhang et al. ("Metal Ion Sensors Based on DNAzymes and Related DNA Molecules" Annual review of analytical chemistry 2011; 4(1):105-128). Chelating agents could also be used as an affinity agent to bind to the target compounds in the device.

Alzheimer's disease can be treated with solanezumab. Rather than administering this drug to a patient, a whole blood treatment device can be used to filter target compounds from whole blood, using the antibody as an affinity agent. Some examples of target compounds for Alzheimer's disease include misfolded amyloid beta and tau proteins.

Bacteria and toxins in the bloodstream can be treated with various drugs. Rather than administering these drugs to a patient, a whole blood treatment device can be used to filter the bacteria or toxins from whole blood. Examples of toxins which could be target compounds include botulinum toxin produced by Clostridium botulinum, Corynebacterium diphtheriae toxin, produced during life-threatening symptoms of diphtheria, and tetanospasmin produced by Clostridium tetani. Antibodies and aptamers may be used as affinity agents for the bacteria or toxins. Such antibodies and aptamers may be prepared by well-known methods.

Various potent cytokines, including tumor necrosis factor (TNF) and interleukin 1, are at increased concentrations in the blood of patients with sepsis. Furthermore, inhibitory checkpoint molecules are also present in increased concentration in the blood of patients with sepsis. These are described in Hotchkiss et al. ("Immunosuppression in sepsis: a novel understanding of the disorder and a new therapeutic approach" *The Lancet infectious diseases.* 2013; 13(3):260-268). A whole blood treatment device can be used to filter the cytokines or inhibitory checkpoint molecules from whole blood. Antibodies and aptamers may be used as affinity agents for the bacteria or toxins.

Methanol poisoning can be treated by competitive inhibition. Methanol concentration could also be reduced using the whole blood treatment device with affinity agents such as aptamers.

Heroin overdoses can be treated by various drugs. Rather than administering these drugs, a whole blood treatment device could be used to reduce the concentration of opioids in the blood. Antibodies, aptamers or other compounds may be used as affinity agents for the opioids.

Methods of making antibodies are well-known in the art. Monoclonal antibodies are usually made by fusing mouse spleen cells immunized with a desired antigen with myeloma cells (B-cell cancer cells, which are known for producing antibodies). The fused cells are transferred to a medium that is selective for fused cells. Several cell cultures are then grown from single parent cells. The antibodies from the different parent cells are then assayed using well-known methods such as ELISA to determine the antibodies ability to bind the antigen.

It would be understood by those skilled in the art, that the systematic evolution of ligands by exponential enrichment (SELEX) technique, or similar techniques, could be used to produce aptamers that specifically bind or target compounds or cells. In the SELEX technique, a large quantity of randomly generated sequences is generated and exposed to the target ligand. The sequences that did not bind the target ligand are removed through affinity chromatography. The sequences that did bind the target ligand are then eluted and amplified by PCR to prepare for subsequent rounds of selection, in order to find the sequence that binds best to the ligand.

The invention claimed is:

1. A whole blood treatment device, comprising:
   a first conduit, a second conduit, and a rotating or reciprocating element having a channel;
   wherein the first and second conduits are fluidly coupled to the rotating or reciprocating element such that the channel is fluidly continuous with the first conduit when the channel is fluidly discontinuous with the second conduit, and such that the channel is fluidly discontinuous with the first conduit when the channel is fluidly continuous with the second conduit;
   wherein the first conduit is configured to receive whole blood, and wherein the second conduit is configured to receive a regeneration fluid; and
   wherein the channel comprises a surface that is modified with an affinity agent at a concentration effective to allow removal of a target compound from whole blood.

2. The whole blood treatment device of claim 1 wherein the rotating or reciprocating element is configured as a wheel having a body with a front and back surface, and wherein the channel extends through the body and fluidly couples the front and back surface.

3. The whole blood treatment device of claim 1 wherein a portion of the rotating or reciprocating element is configured as an Archimedean screw, and wherein the channel is configured as a helical groove.

4. The whole blood treatment device of claim 1 wherein the rotating or reciprocating element is configured as a reciprocating piston having a body with a front and back surface, and wherein the channel extends through the body and fluidly couples the front and back surface.

5. The whole blood treatment device of claim 1 wherein the first conduit has a proximal and a distal end, and wherein proximal and distal ends are configured to fluidly connect to a shunt or blood vessel of a mammal.

6. The whole blood treatment device of claim 1 further comprising a third conduit that is fluidly coupled to an analyzer that is configured to measure quantity of an analyte in the whole blood.

7. The whole blood treatment device of claim 1 further comprising a fourth conduit that is fluidly coupled to a dispensing device that is configured to dispense a measured quantity of a pharmaceutical agent into the whole blood.

8. The whole blood treatment device of claim 1 wherein at least a portion of the first and second conduits and the rotating or reciprocating element are enclosed within a housing.

9. The whole blood treatment device of claim 1 wherein the device is configured as a wearable device.

10. The whole blood treatment device of claim 1 further comprising an actuator that is configured to drive the rotating or reciprocating element.

11. The whole blood treatment device of claim 1 further comprising a control circuit that is configured to drive the actuator as a function of blood pressure.

12. The whole blood treatment device of claim 1, wherein the affinity agent is selected from the group consisting of antibodies, aptamers and small molecules.

13. The whole blood treatment device of claim 1, wherein the target compound is IL-8.

14. The whole blood treatment device of claim 13, wherein the affinity agent is selected from the group consisting of: HuMab 10F8, glycosaminoglycan (GAG) heparin, protease inhibitor alpha2-macroglobulin and Cyclosporin A.

15. The whole blood treatment device of claim 1, wherein the target compound is an inhibitory checkpoint molecule.

16. The whole blood treatment device of claim 1, wherein the target compound is an inflammatory factor.

17. The whole blood treatment device of claim 1, wherein the target compound is selected from the group consisting of: viruses, bacteria and toxins.

18. A method of removing a target compound from whole blood of a mammal in a whole blood treatment device, comprising:
   (a) moving the whole blood through a channel in a rotating or reciprocating element while the channel is fluidly coupled to a first conduit that contains the whole blood;
   wherein the channel comprises a surface that is modified with an affinity agent at a concentration effective to allow removal of a target compound from whole blood;
   (b) moving the rotating or reciprocating element in a position such that the channel is fluidly disconnected from the first conduit and fluidly connected with a second conduit;
   (c) eluting the target compound from the surface while the channel is fluidly connected with the second conduit; and (d) further moving the rotating or reciprocating element in a position such that the channel is fluidly connected with the first conduit and fluidly disconnected with the second conduit.

19. A whole blood treatment device, comprising:
a first conduit, a sealing area, and a rotating or reciprocating element having a channel;
wherein the first conduit is fluidly coupled to the rotating or reciprocating element such that the channel is fluidly continuous with the first conduit when the channel is fluidly discontinuous with the sealing area, and such that the channel is fluidly discontinuous with the first conduit when the channel is fluidly continuous with the sealing area;
wherein the first conduit is configured to receive whole blood, and wherein the sealing area is configured to allow flow-less incubation of the whole blood in the channel when the channel is fluidly continuous with the sealing area; and
wherein the channel comprises a surface that is modified with an affinity agent at a concentration effective to allow removal of a target compound from whole blood.

20. The whole blood treatment device of claim 19 wherein the channel is configured as a replaceable cylinder.

\* \* \* \* \*